United States Patent [19]

Samuelson et al.

[11] Patent Number: 5,792,143
[45] Date of Patent: Aug. 11, 1998

[54] NECK LENGTH MEASURING DEVICE AND METHOD OF USING SAME FOR IMPLANTING A HIP PROSTHESIS

[75] Inventors: Kent M. Samuelson, Salt Lake City, Utah; Kevin T. Stone, Jacksonville, Fla.

[73] Assignee: Biomet, Inc, Warsaw, Ind.; a part interest

[21] Appl. No.: 840,576

[22] Filed: Apr. 21, 1997

[51] Int. Cl.$^6$ .................................................. A61B 17/56
[52] U.S. Cl. ............................................. 606/102; 623/23
[58] Field of Search .............................. 606/102, 89, 88, 606/87, 96, 86; 623/20, 22, 23

[56] References Cited

U.S. PATENT DOCUMENTS

| | | | |
|---|---|---|---|
| 4,959,066 | 9/1990 | Dunn et al. | 606/89 |
| 5,342,366 | 8/1994 | Whiteside et al. | 606/86 |
| 5,578,037 | 11/1996 | Sanders et al. | 606/80 |
| 5,607,431 | 3/1997 | Dudasik et al. | 606/80 |

OTHER PUBLICATIONS

Biomet, Inc., Integral® Hip System, 20 pages, 1995, USA.
Biomet, Inc., RingLoc® Acetabular Series, Reference Chart Low Profile Acetabular Design: Rx 90 Series, 4 pages, 1995, USA.
Biomet, Inc., RingLoc® Acetabular Series, Reference Chart Full Hemisphere Acetabular Design: Peripheral Fixation, 6 pages, 1995, USA.
Biomet, Inc., Healey Flanged Revision Acetabular System, 12 pages, 1993, USA.
Biomet, Inc., Universal® Hip System, RingLoc Acetabular Series, 16 pages, 1993, USA.
Biomet, Inc., The Answer Hip System, Surgical Techniques, 12 pages, 1992, USA.
Biomet, Inc., Bi-Metric Total Hip System, Surgical Technique, 12 pages, 1992, USA.
Biomet, Inc., Alliance Hip System, 20 pages, 1993, USA.
Biomet, Inc., Rx 90® Total Hip System, Femoral Series, 16 pages, 1995, USA.
Biomet, Inc., Impact® Modular Revision, The Impact Modular Revision Hip System, 20 pages, 1995, USA.
Biomet, Inc., Positively Impact Your Clinical Results, Impact® Modular Total Hip System, 24 pages, 1993, USA.
Biomet, Inc., Integral® Hip System, Integral Primary Surgical Technique, 20 pages, 1996, USA.
Biomet, Inc., Hip Fracture System Surgical Technique, 8 pages, 1994, USA.

Primary Examiner—Guy V. Tucker
Attorney, Agent, or Firm—Liell & McNeil

[57] ABSTRACT

A method of implanting a hip prosthesis includes utilization of a device at the implantation site to confirm that the femoral prosthesis will have a neck length corresponding to a preoperative plan. First, a desired neck size for the femoral prosthesis is determined. Then, the femoral prosthesis is positioned in the femur. Next, a locator rod component is advanced toward the femoral prosthesis along an axis parallel to the longitudinal axis of the femoral prosthesis until a greater trochanter locator mounted on the side of the locator rod component is as close as possible to contacting the greater trochanter of the femur. Next, a neck sizing component, which has neck size markings on its outer surface, is placed on the neck projection of the femoral prosthesis. Finally, a reference distance is determined by identifying which of the reference distance markings of the locator rod component corresponds to a desired neck size marking on the neck measuring device along a line substantially perpendicular to the longitudinal axis of the femoral prosthesis. The determined reference distance should correspond to a planned reference distance that was determined in an appropriate preoperative templating and measuring procedure.

17 Claims, 4 Drawing Sheets

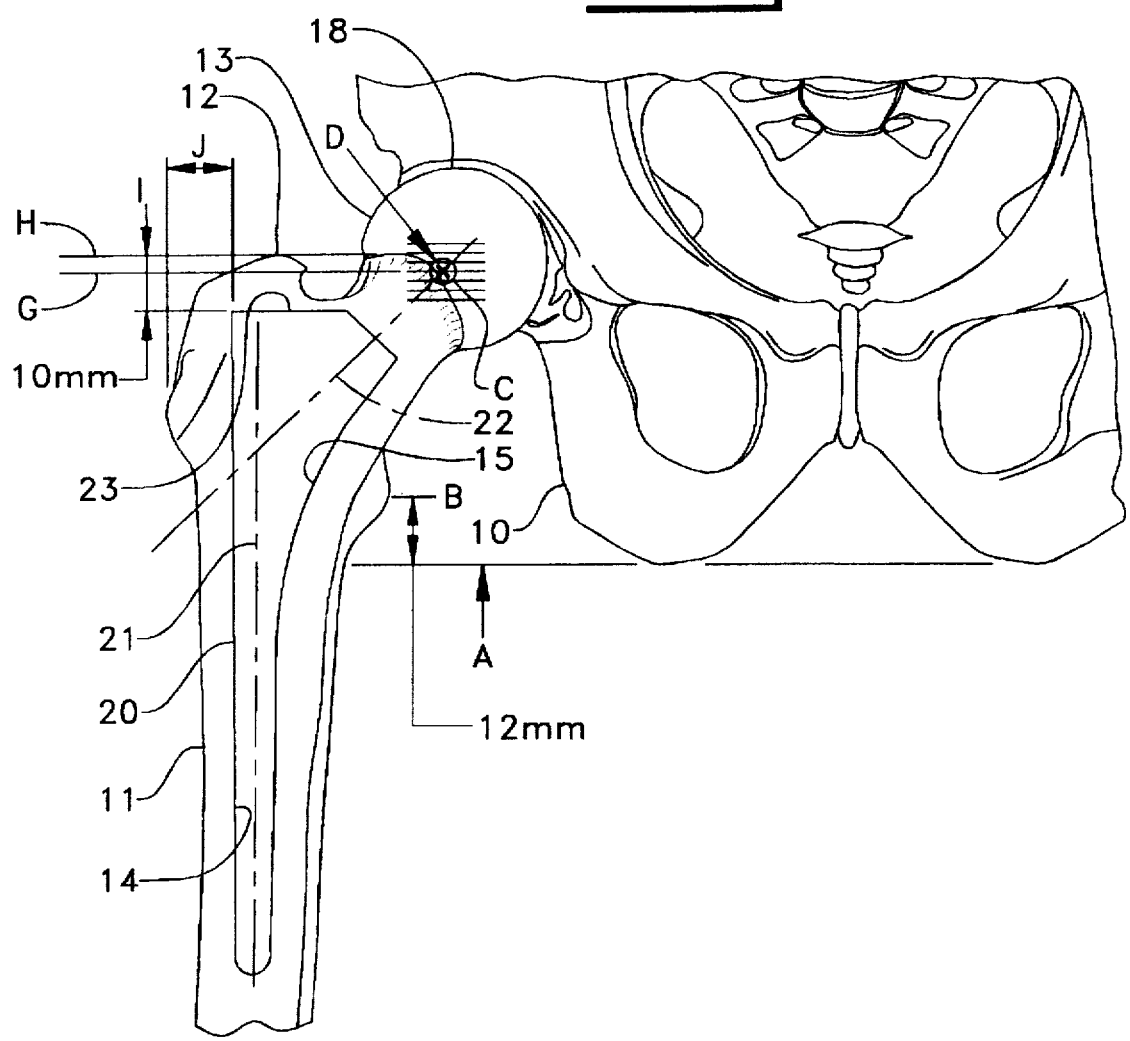

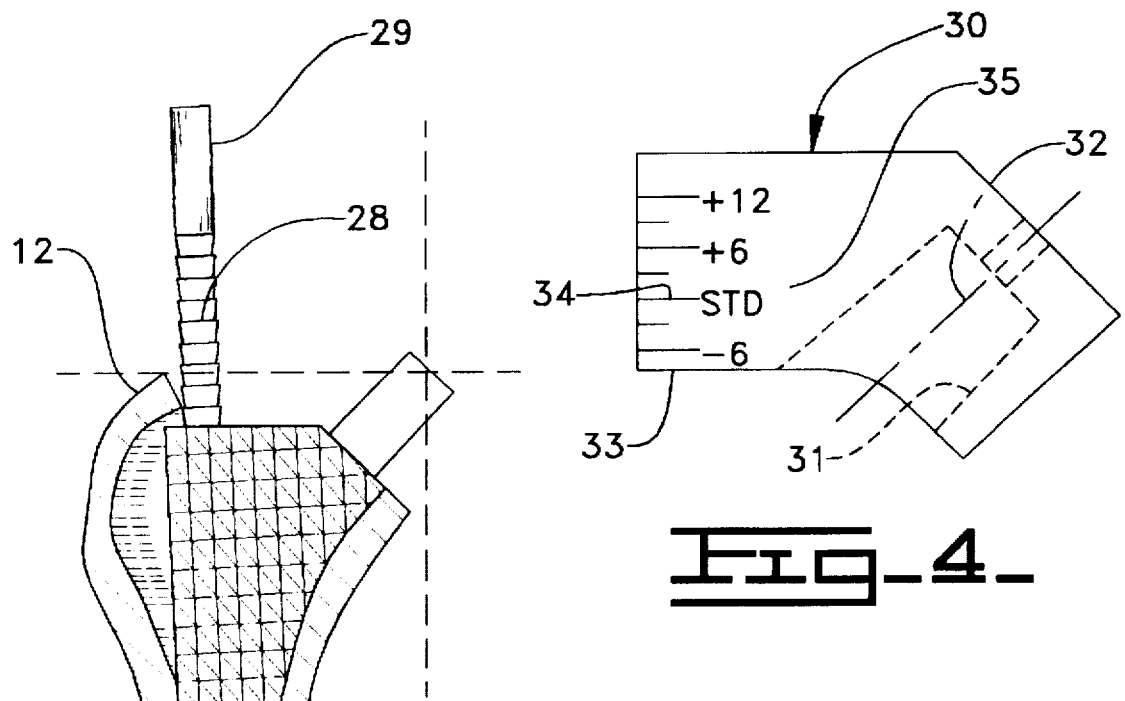
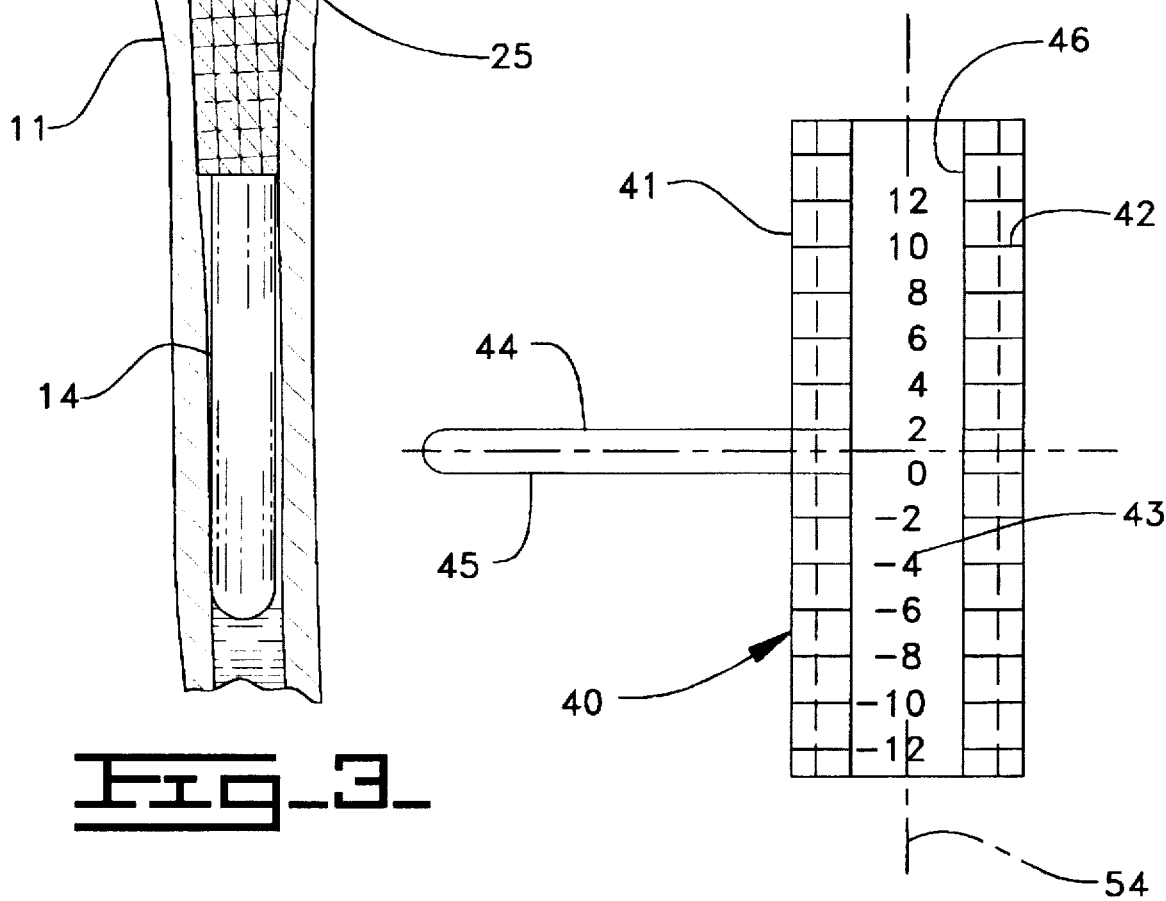

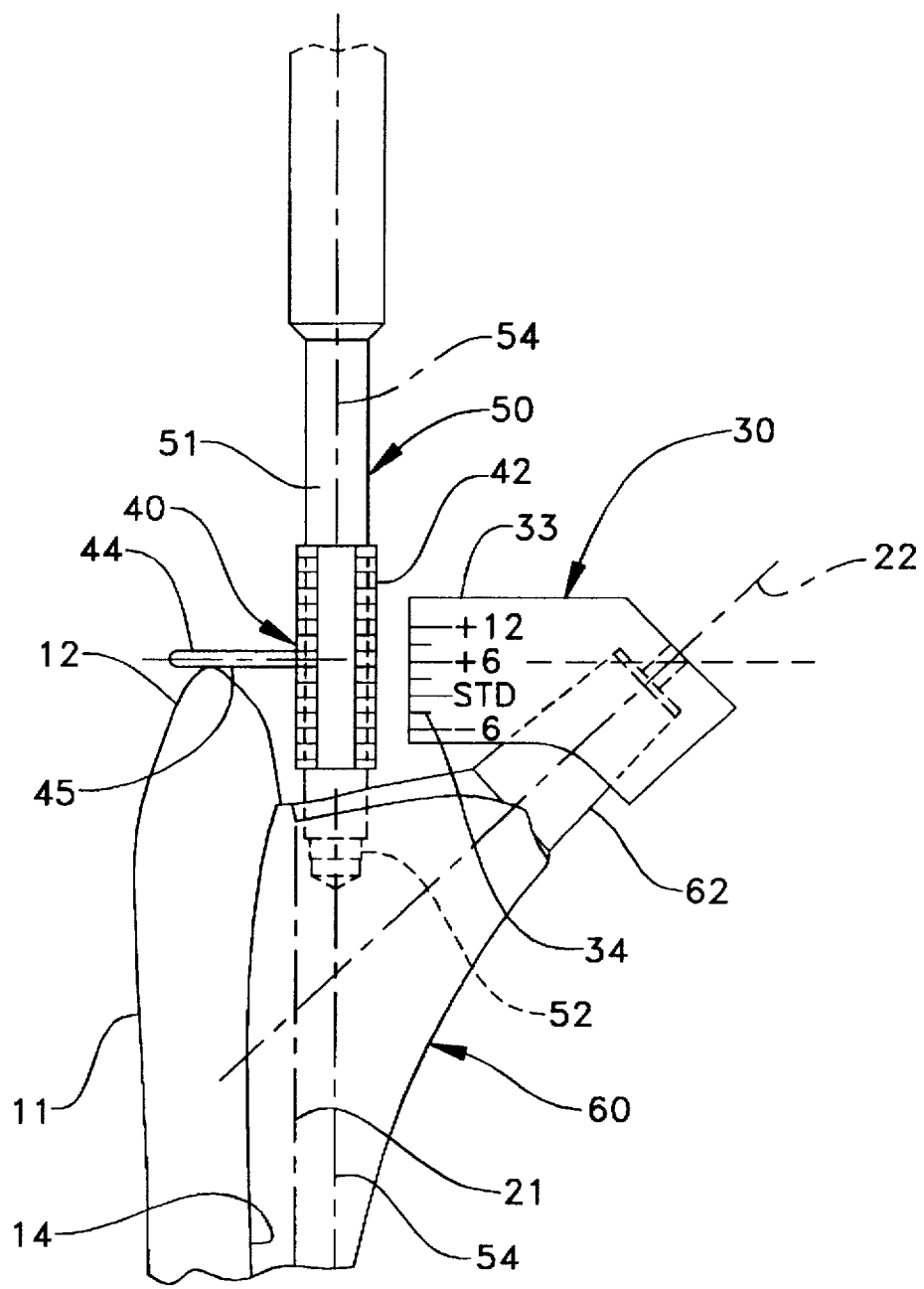

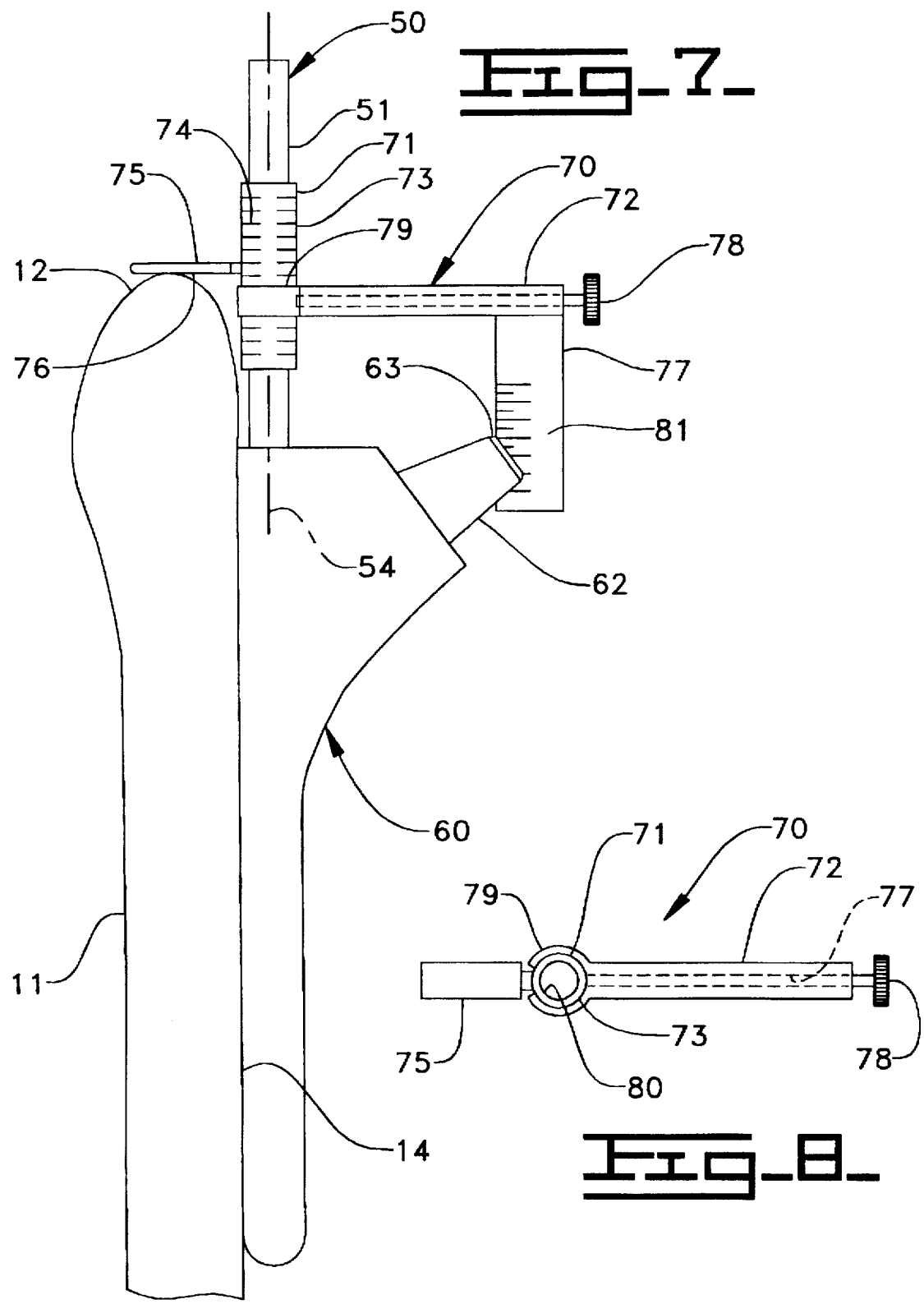

NECK LENGTH MEASURING DEVICE AND METHOD OF USING SAME FOR IMPLANTING A HIP PROSTHESIS

TECHNICAL FIELD

The present invention relates generally to hip replacement surgery, and more particularly to the use of a neck length measuring device during a hip replacement procedure to insure that the correct prosthesis is selected and accurately implanted according to a preoperative plan.

BACKGROUND ART

Hip replacement surgery has long been known in the art. A typical hip replacement surgery begins with a preoperative plan in which x-rays of the patient's hip are taken and an appropriately sized femoral prosthesis is chosen. In choosing a femoral prosthesis, the physician normally takes into account such factors as the internal diameter of the femur, the patient's existing offset distance from the hip socket to the femur centerline, the size of the patient's femur, whether any changes to the patient's existing femoral dimensions are desired and other factors known in the art. A typical hip replacement prosthesis includes a femoral prosthesis having a stem portion, a body and a head, of which the stem and body are embedded in the patient's existing femur after portions of the same have been removed. The head portion of the femoral prosthesis is received in a socket, which includes a hemispherical cavity, that is attached to the patient's pelvis. In many cases, a femoral prosthesis is available in a wide variety of different body sizes and shapes, stem diameters and lengths, and head sizes and lengths. In addition, different heads are available and a wide variety of femoral neck lengths can be accomplished through various combinations of different heads and bodies.

While good preoperative planning can allow a physician to accurately determine a precise matched fit for a femoral prosthesis, the overall success of the operation requires that the chosen femoral prosthesis be implanted precisely as planned. This aspect of hip replacement surgery has proven somewhat more problematic. For instance, a physician may well have chosen the proper femoral prosthesis for a particular patient, but if that prosthesis is implanted as much as a few millimeters away from its planned location, the outcome of the hip replacement surgery will inevitably be less than a complete success and some unnecessary complications can follow, such as over stressing or unevenness between the left and right hip.

One of the most critical aspects of hip replacement surgery relates to insuring that the neck length and head offset distance of the femoral prosthesis upon implantation is as close as possible to the preoperative plan. Neck length generally refers to the distance from the base of the neck projection or taper of the body portion of the femoral prosthesis to the center of the head. Head offset is generally referred to as the distance from the stem centerline to the center of the head. A standard neck length is generally referred to in the industry as one having a distance of about 34 millimeters in length. However, in some cases neck length can be as much as 12 millimeters greater than the standard or as short as 6 millimeters less than the standard neck length. Those skilled in the art will appreciate that the actual neck length of the bone/implant restoration can vary significantly depending upon the depth at which the femoral prosthesis is implanted in the femur. Thus, the art is in need of a means by which the desired neck length can be confirmed relative to the preoperative plan at the time of implantation in order to achieve the best overall success with the hip replacement surgery.

SUMMARY OF THE INVENTION

A method of implanting a hip prosthesis comprises the initial step of determining a desired neck size for a femoral prosthesis having a longitudinal axis and a neck projection. The femoral prosthesis is then positioned in the femur, which has a greater trochanter. A locator rod component, which has reference distance markings on its side and a greater trochanter locator, is advanced toward the femoral prosthesis along an axis parallel to the longitudinal axis of the prosthesis until the greater trochanter locator is contacting the greater trochanter of the femur. A neck sizing component, which has neck sizing markings on its outer surface, is then positioned adjacent the neck projection of the femoral prosthesis. Finally, the physician determines a reference distance by identifying which of the reference distance markings of the locator rod component corresponds to a desired neck size marking on the neck measuring device along a line substantially perpendicular to the longitudinal axis of the femoral prosthesis. This procedure allows the physician to confirm that the actual implanted femoral prosthesis has a neck size corresponding to that of his or her preoperative plan.

In another embodiment of the present invention, a neck length measuring device is utilized for use in implanting a hip prosthesis having a longitudinal axis and a neck projection formed at a neck angle with respect to the longitudinal axis. The neck length measuring device includes a locator rod component having a side and a long axis, and a plurality of reference distance markings on its side along its long axis. The locator rod component also has a greater trochanter locator attached to its side. A neck sizing component has an outer surface with a plurality of neck size markings distributed along a line substantially parallel to said long axis.

BRIEF DESCRIPTION OF THE DRAWINGS

FIG. 1 is a front elevational view of a hip and femur utilized in illustrating a preoperative planning procedure according to one aspect of the present invention.

FIG. 2 is an example preoperative planning worksheet according to one aspect of the present invention.

FIG. 3 is a side elevational view of a broaching portion of a hip replacement procedure according to one aspect of the present invention.

FIG. 4 is a side elevational view of a neck sizing component according to the present invention.

FIG. 5 is a side elevational view of a locator rod component according to the present invention.

FIG. 6 is a side elevational view of a femur and femoral prosthesis utilizing a neck length measuring device at an implantation site according to the present invention.

FIG. 7 is a side elevational view of a femur and femoral prosthesis utilizing a neck length measuring device at an implantation site according to another embodiment of the present invention.

FIG. 8 is a top view of the neck length measuring device shown in FIG. 7.

DETAILED DESCRIPTION OF THE PREFERRED EMBODIMENTS

The preoperative planning procedure according to the present invention typically begins by taking appropriate x-rays of the hip and femur area to be replaced (see FIG. 1). On the x-ray, a vertical line 21 is drawn through the femur which corresponds to the longitudinal axis of the femur and the longitudinal axis of a femoral prosthesis to be implanted. Next, a line 22 is drawn along the neck of the femur 11 that intersects longitudinal axis 21. Line 22 represents the centerline of the existing femur's neck as well as the intended centerline of the forthcoming neck projection of the femoral prosthesis to be implanted.

On the x-ray, the physician next draws a line A across the inferior borders of the ischia (the inferior ischial line). A horizontal line B is then drawn parallel to line A through either the centers or the inferior margins of the lesser trochanter of femur 11. Next, the physician measures the distances from the inferior ischial line A to line B on both femurs. After correlating with clinical examination and comparing the same to this distance, an estimated limb length difference should be entered at item 3 of the example preoperative planning worksheet shown in FIG. 2. If the lesser trochanters are not well visualized, the distances from the inferior ischial line A to the proximal tips of the greater trochanter 12 can be substituted.

Next, the position of the acetabular or head component is marked with an "o" at its center of rotation point C along line 22. An exact size determination is not necessary at this time. Next, the hemispherical outline 18 is drawn on the x-ray corresponding to the current outer surface of the patient's existing femoral head. The position of the new femoral head location relative to the femur is marked with an "x" along line 22, which corresponds to location D on FIG. 1. If the side to be replaced is short, the "x" will be proximal to the "o" of location C by the measurement from item 3 of the worksheet shown in FIG. 2. If the side to be replaced is long, the "x" will be distal to the "o" by the measurement from item 3 of the worksheet. Those skilled in the art will appreciate that care must be taken when shortening the total hip replacement since shortening can result in instability. The physician then selects a femoral template that gives the best possible fit to the patient's femur 11. Proper fitting is normally accomplished by positioning the template under or over the x-ray so that the stem diameter (diaphyseal fit) of the template fits closely within the available medullary canal 14 of the patient's femur 11.

It should be noted that metaphyseal fit 15 is more important than distal fit. Furthermore and ideally, a planned neck length should be in the midrange from minus 3 millimeters to plus 3 millimeters away from the standard neck length since this allows for the maximum adjustment at the time of surgery. This may sometimes need to be varied in severe cases of coxa vara or coxa valga where the neck angle varies from the standard 135°. A variation of three millimeters in neck length generally results in a vertical and horizontal displacement of the stem on the order of about 2 millimeters. If the stem position requires a neck length outside of the range of minus 3 to plus 3 millimeters from the standard neck length, the physician should consider going to the next larger or smaller stem size. The depth to which the stem seats in the femur generally varies by about 6 to 10 millimeters between sizes. The physician should then enter the selected stem size at item 4 on the example worksheet shown in FIG. 2.

Utilizing a template corresponding to the desired stem size, the outline of the femoral prosthesis from the template is then traced onto the x-ray at its intended implantation location. Next, a line G, which is perpendicular to longitudinal axis 21, is drawn from the center of the desired head location "x" through the greater trochanter 12. Next, a short horizontal line H, which is perpendicular to long axis 21 and parallel to G, is drawn at the proximal most tip of the greater trochanter 12. The physician then measures the desired reference distance between lines H and G. If the center of the desired head location is below the tip of the trochanter, this measurement should be proceeded by a "−" sign. If the center of the desired head location is above the tip of the greater trochanter, the measurement should be proceeded by a "+" sign. This number is recorded at item 5 as the "tip-to-x" distance and is recorded on the preoperative planning worksheet of FIG. 2. Next, the physician measures the desired depth distance from the tip of greater trochanter 12 to the outlined top 23 of the femoral prosthesis that is traced onto the x-ray. This number is recorded at item 6 of the pre-planning worksheet as the "tip-to-top" distance.

Next, the physician measures the distance J from the lateral most margin of the greater trochanter to the lateral edge of the stem. This number is recorded at item 7 on the pre-planning worksheet. Correlating this distance with the measurement at surgery insures correct varus-valgus positioning of the femoral prosthesis. Utilizing the template and the various lines drawn on the x-ray, the physician next determines what desired neck length would be suitable for the hip replacement surgery. In the example shown in FIG. 1, the desired neck length would be plus 3 millimeters since the template indicates a plus 3 millimeters neck length from location "x". The desired neck size is recorded at item 8 on the pre-planning worksheet.

At the time of surgery, if the femoral prosthesis is seated to a depth equal to the measurement "tip-to-top" (desired depth distance), the measurement "tip-to-x" (desired reference distance) should correspond to the actual reference distance measurement at surgery for that particular neck length. Again, it should be noted that variations of about 2 millimeters in depth can alter the neck length by about 3 millimeters if measurements were all done correctly.

The actual hip replacement surgery is begun by any standard approach that exposes the hip. The femoral neck is then cut at approximately the level determined from the preoperative planning. The exact level is not critical but if the neck is left too long, there is the risk of impingement between the femoral neck and the pelvis or the head component of the femoral prosthesis. If the neck is cut too short, excess bone is needlessly removed and some torsional stability of the femoral prosthesis is lost. The preoperative planning will show how much of the proximal end of the femoral prosthesis will have to be lateralized into the region of the greater trochanter. A gouge should be used to remove the dense cortical bone which is the small remnant of the superolateral portion of the femoral neck and some of the medial margin of the greater trochanter. A canal finder is then inserted into the medullary canal 14 in a conventional manner. Next, the medullary canal is reamed with steadily larger reamers until the desired size for the chosen stem is reached before any broaching is started.

After reaming, successive broaches are used in sequence until the planned size is reached. The correct anteversion is determined by lining up the most medial part of the broach with the calcar. This usually results in the posterior surface of the broach being parallel with the posterior cortex of the neck. When the physician has stepped up to a broach 25 as shown in FIG. 3 that corresponds to the desired femoral prosthesis 60 (FIG. 6), a broach measuring device 29 is threaded into the superolateral portion of the broach. The broach measuring device includes distance measurement markings 28 on its outer surface on the order of about 2 millimeter increments. The depth of the broach is noted relative to the level of the tip of the greater trochanter 12. The depth of broach 25 should correspond to the "tip-to-top" (desired depth distance) distance recorded at line 6 in the preoperative planning worksheet.

If a tight fit is achieved with a smaller broach than indicated in initial planning, it may be necessary to go to a smaller size prosthesis. The surgeon should ascertain that the broach is lateralized properly and is not tight due to incorrect varus placement. If placement is correct, the smaller size should be used. Reaming the distal canal of femur 11 one size larger than the femoral prosthesis implant 60 is not a problem since proximal fixation is the goal. Conversely, if the broach of the planned size seats deeper than planned, the canal should be prepared for the next larger size. These variations in size can result from slight inaccuracies in templating and variations in bone density from patient to patient. Next, the acetabulum is exposed by any standard approach and reamed in a conventional manner. If necessary, a central peg hole can be drilled. After appropriate irrigation and inspection, the acetabular cup is inserted and fixed into position, followed by insertion of an appropriate liner.

After acetabular cup insertion, the broach may be re-inserted and a trial reduction performed, or one can move directly to inserting the femoral prosthesis 60. A femoral inserter 50 is threaded into femoral prosthesis 60 at location 52, and the femoral prosthesis is inserted into the canal of the femur 11. Femoral inserter 50 preferably includes depth graduation marks on its outer surface 51, which cannot be seen in FIG. 6. These marks correspond to the marks on a depth scale used on the broach measuring device 29 of FIG. 3. This is utilized to confirm that the implant will seat to the same level of its corresponding broach and according to the desired depth distance of the preoperative plan. An optional bullet tip stem inserter with the same graduation marks can also be utilized.

Next, the appropriate neck length is established with the neck measuring device illustrated in FIGS. 4, 5 and 6, or the alternative device illustrated in FIGS. 7 and 8. With regard to FIGS. 4–6, the neck length measuring device includes a locator rod component 40 having a side 41 and a long axis 54. A plurality of reference distance markings 42 are made along the side of long axis 54, preferably in 2 millimeter increments. Locator rod component 40 also includes a greater trochanter locator 44 attached to its side 41 that includes a locating surface 45 that is positioned away from and substantially perpendicular to long axis 54. Numerical distance markings 43 are also included on side 41 such that a zero marking corresponds to locating surface 45, negative markings are below the locating surface and positive markings are above locating surface 45. Locator rod component 46 also preferably includes a central bore 46 that allows it to be slidably received on the shaft 51 of femoral inserter 50 (FIG. 6).

The neck length measuring device also includes a neck sizing component 30 (FIG. 4) that defines a cavity 31 with a centerline 32 that is sized to be received on a neck projection or taper 62 of the femoral prosthesis 60. Neck sizing component 30 also includes an outer surface in the form of a flag portion 33 having a plurality of neck size markings 34 and corresponding size identifiers 35 engraved thereon. The neck size markings 34 are distributed vertically along a line that is substantially parallel to long axis 54 when neck sizing component 30 is mounted on or otherwise positioned adjacent neck projection 62.

Confirming the appropriate neck length is accomplished in the following manner. The locator rod component is mounted on the shaft 51 of femoral inserter 50. The femoral inserter 50 is again threaded at location 52 into femoral prosthesis 60 and locator surface 45 is moved into a position that is contacting the tip of the greater trochanter 12 of the femur 11. The neck sizing component 30 is then placed on or otherwise positioned adjacent the neck projection 62 of femoral prosthesis 60 so that flag portion 33 points in the direction of the longitudinal axis 21 of the prosthesis. The locator rod component 40 moves along an axis 54 that is substantially parallel to the longitudinal axis 21 of the femoral prosthesis 60. In order to confirm that the femoral prosthesis 60 is implanted at the desired location as per the preoperative plan, the desired reference distance marking on the locator rod component and the desired neck size marking 34 on the neck sizing component 30 should correspond to the "tip-to-x" distance (desired reference distance) recorded at line 5 of the preoperative planning worksheet shown in FIG. 2. FIG. 6 shows that the minus 2 millimeter distance on the locator rod component indeed corresponds to the plus 3 millimeter neck size on the neck length component thus confirming that femoral prosthesis 60 is located as per the preoperative plan.

After confirming the appropriate sizing and location, the modular femoral head (not shown) which corresponds to the desired neck size, is attached to neck projection 62 of femoral prosthesis 60. Trial reduction with trial heads can be performed to assure that proper leg length and stability have been achieved. With the appropriate modular femoral head impacted onto neck projection 62, the hip is now ready to be reduced. After the hip is reduced, it is taken through a range of motion to check for adequate motion and stability. The remaining closure can be done in a routine fashion.

Referring now to FIG. 7 and 8, a neck length measuring device 70 according to another embodiment of the present invention is shown being utilized to confirm that the appropriate neck length has been accomplished. Unlike the two part neck length measuring device of FIGS. 4–6, neck length measuring device 70 includes a locator rod component 71 and a neck sizing component 72 slidably mounted thereon. Like the earlier embodiment, locator rod component 71 includes a greater trochanter locator 75 attached to its side 73. Like the earlier embodiment, a plurality of reference distance markings are etched on side 73 such that the zero marking corresponds to locating surface 76. Locator rod component 71 also includes a central bore 80 that allows it to be slidably received on the shaft 51 of femoral inserter 50.

Neck sizing component 72 has an outer surface with a plurality of neck size markings 81 distributed along a line that is substantially parallel to long axis 54. Neck sizing component 72 also includes a set screw 78 that allows the relative positioning of locator rod component 71 and neck sizing component 72 to be fixed. In this case, since line 3 of the preoperative plan showed a desired limb length difference of negative 2 millimeters, the top edge of neck sizing component 72 is lined up with the minus 2 millimeter marking on the locator rod component 71 and fixed into place with set screw 78. Neck sizing component 72 also includes a flag shaped portion 77 that includes a plurality of neck size markings 81 distributed along a line that is substantially parallel to long axis 54. In this embodiment, neck measuring device keys off of the small bevel 63 at the end of neck projection 62, as opposed to a predetermined match fit between neck projection 62 and cavity 31 of the previous embodiment. As per the preoperative plan, neck measuring device 70 confirms that femoral prosthesis 60 is properly positioned since the bevel 63 corresponds to a neck size of plus 3 millimeters, as per the preoperative plan. In other words, when flag shaped portion 77 is positioned adjacent neck projection 62, bevel 63 confirms that the femoral prosthesis 60 is properly implanted at the desired location because the bevel corresponds to the plus 3 millimeter neck size when the neck sizing component is positioned at the minus 2 millimeter desired reference distance on the locator rod component.

It should be understood that the above description is intended for illustrative purposes only, and is not intended to limit the scope of the present invention in any way. For instance, those skilled in the art will appreciate that various modifications can be made to the neck measuring device of the present invention without departing from the spirit and scope of its intended purpose. For instance, those skilled in the art will appreciate that a neck measuring device according to the present invention can come in a wide variety of shapes, and include one or more separate or attached components, and still accomplish the neck measuring goal of the present invention. In any event, the scope of the present invention should be determined in terms of the claims as set forth below.

We claim:

1. A method of implanting a hip prosthesis comprising the steps of:

determining a desired neck size for a femoral prosthesis having a longitudinal axis and a neck projection;

positioning said femoral prosthesis in a femur having a greater trochanter;

advancing an end of a locator rod component, which has reference distance markings on a side and a greater trochanter locator, toward said femoral prosthesis along an axis parallel to said longitudinal axis until said greater trochanter locator is contacting said greater trochanter of said femur;

positioning a neck sizing component, which has neck size markings, adjacent said neck projection of said femoral prosthesis;

determining a reference distance by identifying which of said reference distance markings of said locator rod component corresponds to a desired neck size marking on said neck sizing component along a line substantially perpendicular to said longitudinal axis.

2. The method of implanting a hip prosthesis according to claim 1 wherein said step of determining a desired neck size includes a step of determining a desired reference distance along said longitudinal axis from said greater trochanter to a new femoral head location.

3. The method of implanting a hip prosthesis according to claim 2 further comprising a step of:

attaching a modular femoral head, which corresponds to said desired neck size, to said neck projection of said femoral prosthesis if said reference distance is about equal to said desired reference distance.

4. The method of implanting a hip prosthesis according to claim 3 wherein said step of determining a desired neck size further includes the steps of:

determining a limb length difference distance for a hip to be replaced with said hip prosthesis;

determining a desired stem size for said femoral prosthesis; and determining a desired depth distance along said longitudinal axis from said greater trochanter to a top of said femoral prosthesis.

5. The method of implanting a hip prosthesis according to claim 4 further comprising the steps of:

broaching said femur until a broach corresponding to said desired stem size is positioned in said femur at a depth about equal to said desired depth distance;

removing said broach from said femur; and positioning said femoral prosthesis in said femur to a depth about equal to said desired depth distance.

6. The method of implanting a hip prosthesis according to claim 5 wherein said step of determining a desired neck size further includes the steps of:

making an X-ray of said hip;

marking said new femoral head location on said X-ray;

drawing an outline of said femoral prosthesis on said X-ray;

drawing a first line perpendicular to said longitudinal axis through said new femoral head location on said X-ray;

drawing a second line perpendicular to said longitudinal axis along a tip of said greater trochanter on said X-ray.

7. A combination neck length measuring device and hip prosthesis comprising:

a hip prosthesis having a longitudinal axis and a neck projection formed at a neck angle with respect to said longitudinal axis a locator rod component having a side and a long axis parallel to said longitudinal axis, and said side having a plurality of reference distance markings along said long axis, and having a greater trochanter locator attached to said side, and said locator rod component being positioned adjacent said hip prosthesis; and a neck sizing component mounted on said neck projection and having an outer surface with a plurality of neck size markings distributed along a line substantially parallel to said long axis.

8. The combination neck length measuring device and hip prosthesis of claim 7 wherein said greater trochanter locator has a locating surface positioned away from, and substantially perpendicular to, said long axis.

9. A neck length measuring device for use in implanting a hip prosthesis having a longitudinal axis and a neck projection formed at a neck angle with respect to said longitudinal axis comprising:

a locator rod component having a side and a long axis, and said side having a plurality of reference distance markings along said long axis, and having a greater trochanter locator attached to said side, and said greater trochanter locator having a locating surface positioned away from, and substantially perpendicular to, said long axis, and said locator rod component has a longitudinal bore along said long axis sized to slidably receive a femoral inserter therethrough; and a neck sizing component having an outer surface with a plurality of neck size markings distributed along a line substantially parallel to said long axis.

10. The neck length measuring device of claim 9 wherein said reference distance markings include a zero marking corresponding to said locating surface.

11. The neck length measuring device of claim 10 wherein said neck size markings are located on a flag shaped portion of said outer surface.

12. The neck length measuring device of claim 11 wherein said neck sizing component defines a cavity that is sized to receive said neck projection.

13. The neck length measuring device of claim 12 wherein said flag shaped portion projects toward said longitudinal axis when said neck sizing component is mounted on said neck projection.

14. The neck length measuring device of claim 11 wherein said locator rod component is unattached and separate from said neck sizing component.

15. The neck length measuring device of claim 11 wherein said locator rod component is attached to said neck sizing component.

16. The neck length measuring device of claim 15 wherein said neck sizing component is slidably mounted on said locator rod component to move along said long axis.

17. The neck length measuring device of claim 16 wherein said neck sizing component includes a set screw capable of fixing a position of said neck sizing component relative to said locator rod component.

\* \* \* \* \*